(12) United States Patent
Wright

(10) Patent No.: US 7,650,790 B2
(45) Date of Patent: Jan. 26, 2010

(54) METHOD OF INSPECTING A COMPONENT AND AN APPARATUS FOR INSPECTING A COMPONENT

(75) Inventor: David C Wright, Loughborough (GB)

(73) Assignee: Rolls-Royce PLC, London (GB)

(*) Notice: Subject to any disclaimer, the term of this patent is extended or adjusted under 35 U.S.C. 154(b) by 378 days.

(21) Appl. No.: 11/882,858

(22) Filed: Aug. 6, 2007

(65) Prior Publication Data

US 2008/0041160 A1  Feb. 21, 2008

(30) Foreign Application Priority Data

Aug. 15, 2006 (GB) .................. 0616164.0

(51) Int. Cl.
*G01N 29/48* (2006.01)
*G01B 5/28* (2006.01)

(52) U.S. Cl. .............. 73/622; 73/593; 73/599; 73/602; 702/35

(58) Field of Classification Search ............. 73/593, 73/599, 600, 602, 622, 627, 628; 702/35, 702/36, 39
See application file for complete search history.

(56) References Cited

U.S. PATENT DOCUMENTS

| | | | |
|---|---|---|---|
| 2,150,922 A | | 3/1939 | Hay |
| 3,400,578 A | * | 9/1968 | Frarey et al. ............. 73/112.01 |
| 4,065,960 A | * | 1/1978 | Grabendorfer et al. ........ 73/609 |
| 4,332,016 A | * | 5/1982 | Berntsen ........................ 367/7 |
| 4,452,079 A | * | 6/1984 | Tiller ............................ 73/488 |
| 4,517,152 A | * | 5/1985 | Pieper et al. ................. 376/252 |
| 4,558,311 A | * | 12/1985 | Forsgren et al. ............. 340/680 |
| 5,063,779 A | * | 11/1991 | Landry et al. ................. 73/622 |
| 5,654,510 A | * | 8/1997 | Schneider .................... 73/622 |
| 5,942,690 A | * | 8/1999 | Shvetsky ...................... 73/660 |
| 6,396,195 B1 | * | 5/2002 | Lindblad et al. ......... 310/323.19 |

FOREIGN PATENT DOCUMENTS

| | | |
|---|---|---|
| GB | 868258 A | 5/1961 |
| GB | 946590 A | 1/1964 |
| GB | 2 114 758 A | 8/1983 |

* cited by examiner

*Primary Examiner*—J M Saint Surin
(74) *Attorney, Agent, or Firm*—Oliff & Berridge, PLC

(57) ABSTRACT

An apparatus for ultrasonically inspecting a component comprises a first ultrasonic transducer for transmitting an ultrasonic signal into a component having rotational symmetry and a second ultrasonic transducer for detecting the reflected, or transmitted, ultrasonic signal. A motor and a turntable produce relative rotation between the rotationally symmetrical component and the first and second transducers. Motors, a carriage and tracks on a frame provide relative radial motion between the rotationally symmetrical component and the first and second transducers to scan the whole of a surface of the rotationally symmetrical component. An ultrasonic signal analyzer analyses the detected ultrasonic signal by monitoring for ultrasonic signals having an amplitude above a predetermined amplitude and not having rotational symmetry and a display provides an indication that any detected ultrasonic signals above the predetermined amplitude and not having rotational symmetry is a potential flaw in the component.

23 Claims, 5 Drawing Sheets

Position A

0                                                                    360

ST

YZ

Position B

0                                                                    360

ST

WX

YZ

Position C

0                                                                    360

ST

WX

Position D
0

ST

WX

UV

Position E
0                                                                                                   360

ST

DEFECT

UV

METHOD OF INSPECTING A COMPONENT AND AN APPARATUS FOR INSPECTING A
COMPONENT

The present invention relates to a method and an apparatus for inspecting a component, in particular to a method and an apparatus for ultrasonically inspecting a rotationally symmetrical component, for example a turbine disc, a compressor disc, a wheel.

It is known to ultrasonically inspect turbine discs. The turbine disc is placed in a tank of an acoustic couplant, e.g. water, and the turbine disc is rotated about its axis and an ultrasonic probe is moved radially in incremental steps to achieve full coverage of the turbine disc. The ultrasonic probe operates in a pulse echo mode to transmit ultrasound into the turbine disc and to detect reflected ultrasound. The reflected ultrasound is converted to an electric signal and electric signal levels above a predetermined threshold level are assessed to determine if there is a flaw, or defect, in the turbine disc. The electric signal is converted to a signal on a flaw detector screen. The ultrasonic probe may be used to inspect the turbine disc at three angles, 90°+/−5°, to the surface of the turbine disc to cater for potential defect orientations variations.

Currently there are two methods of ultrasonic inspection.

In the first method of ultrasonic inspection, manual inspection, the rotation of the turbine disc, the movement of the ultrasonic probe and the calibration and set up of the ultrasonic probe and interpretation of the electric signal to determine if there is a flaw in the turbine disc are under manual control. An inspector assesses the electric signals on the flaw detector screen throughout the duration of the ultrasonic inspection to determine if there is a flaw in the turbine disc. The inspector carrying out the ultrasonic inspection manually records all the inspection results.

In the second method of ultrasonic inspection, semi-automatic inspection, the rotation of the turbine disc and the movement of the ultrasonic probe are either under manual control or under microprocessor control. The ultrasonic probe is calibrated and set up manually. A programmable distance amplitude correction (DAC) system is employed to compensate for sensitivity change due to depth and material attenuation. An inspector sets up electronic gates at selected positions with predetermined threshold levels. Electric signals with an amplitude greater than the threshold levels are recognised by the electronic gates as potential flaws. The electronic gates detect amplitudes above the threshold level and set of an alarm and stop the ultrasonic inspection. An inspector then assesses the electric signals on the flaw detector screen to determine if there is a flaw in the turbine disc at that position. The semi-automatic inspection process is then restarted. The inspector carrying out the ultrasonic inspection manually records all the inspection results.

The existing method of ultrasonic inspection of the turbine disc has no permanent record of the ultrasound interactions. No auditable data can be retained, no reworking or automatic treatment of the ultrasonic inspection data is possible.

If the automated scan is allowed to traverse positions of abrupt change in turbine disc cross-section multiple ultrasound reflections are received from either side of the step change in cross-section and from the edge itself. These would trigger an alarm. As a result any changes in turbine disc cross-section must be traversed slowly, with the automatic system disabled, with the inspector viewing and interpreting the electric signals manually. Multiple cross-section changes in the turbine disc are present in real components and therefore dictate multiple manual inspections consuming large amounts of inspector time and preventing multi-manning, e.g. one inspector operating more than one ultrasonic inspection system.

Accordingly the present invention seeks to provide a novel apparatus and method of inspecting a component, which reduces, preferably overcomes, the above-mentioned problem.

Accordingly the present invention provides a method of inspecting a component comprising transmitting a signal from a first transducer into a component having rotational symmetry, detecting the reflected, or transmitted, signal by a second transducer, producing relative rotation between the rotationally symmetrical component and the first and second transducers, producing relative radial motion between the rotationally symmetrical component and the first and second transducers to scan the whole of a surface of the rotationally symmetrical component and analysing the detected signal by monitoring for signals having an amplitude above a predetermined amplitude and not having rotational symmetry and providing an indication that any detected signals above the predetermined amplitude and not having rotational symmetry is a potential flaw in the component.

Preferably the present invention provides a method of ultrasonically inspecting a component comprising transmitting an ultrasonic signal from a first transducer into a component having rotational symmetry, detecting the reflected, or transmitted, ultrasonic signal by a second ultrasonic transducer, producing relative rotation between the rotationally symmetrical component and the first and second transducers, producing relative radial motion between the rotationally symmetrical component and the first and second transducers to scan the whole of a surface of the rotationally symmetrical component and analysing the detected ultrasonic signal by monitoring for ultrasonic signals having an amplitude above a predetermined amplitude and not having rotational symmetry and providing an indication that any detected ultrasonic signals above the predetermined amplitude and not having rotational symmetry is a potential flaw in the component.

Preferably the method comprises rotating the component about its axis of symmetry.

Preferably the method comprises moving the first and second transducers radially relative to the component.

Preferably the first transducer is the second transducer.

Preferably the component is a turbine disc, a turbine disc forging, a compressor disc, a compressor disc forging, a fan disc, a fan disc forging, an integrally bladed disc, an integrally bladed disc forging, a wheel, a tube or a shaft.

Preferably the component comprises a metal, a ceramic, a metal matrix composite or a polymer matrix composite.

Preferably the method comprises immersing the component in an acoustic coupling liquid.

Preferably the first transducer is a piezoceramic transducer, an electromagnetic acoustic transducer or a transducer comprising a laser.

Preferably the method comprises producing relative rotation at a constant speed. Preferably the method comprises producing relative rotation at a constant speed between 3 rpm and 30 rpm and more preferably the method comprises producing relative rotation at a constant speed between 20 rpm and 30 rpm.

Alternatively the first transducer is an electromagnetic eddy current transducer.

The present invention also provides an apparatus for inspecting a component comprising a first transducer for transmitting a signal into a component having rotational symmetry, a second transducer for detecting the reflected, or transmitted, signal, means to produce relative rotation between the rotationally symmetrical component and the first and second transducers, means to produce relative radial motion between the rotationally symmetrical component and the first and second transducers to scan the whole of a surface of the rotationally symmetrical component and means to analyse the detected signal by monitoring for signals having an amplitude above a predetermined amplitude and not having rotational symmetry and means to provide an indication that any detected signals above the predetermined amplitude and not having rotational symmetry is a potential flaw in the component.

Preferably the apparatus is for ultrasonically inspecting a component comprising a first ultrasonic transducer for transmitting an ultrasonic signal into a component having rotational symmetry, a second ultrasonic transducer for detecting the reflected, or transmitted, ultrasonic signal, means to produce relative rotation between the rotationally symmetrical component and the first and second transducers, means to produce relative radial motion between the rotationally symmetrical component and the first and second transducers to scan the whole of a surface of the rotationally symmetrical component and means to analyse the detected ultrasonic signal by monitoring for ultrasonic signals having an amplitude above a predetermined amplitude and not having rotational symmetry and means to provide an indication that any detected ultrasonic signals above the predetermined amplitude and not having rotational symmetry is a potential flaw in the component.

Preferably the means to produce relative rotation comprises means to rotate the component about its axis of symmetry.

Preferably the means to produce relative radial motion comprises means to move the first and second transducers radially relative to the component.

Preferably the first transducer is the second transducer.

Preferably the component is a turbine disc, a turbine disc forging, a compressor disc, a compressor disc forging, a fan disc, a fan disc forging, an integrally bladed disc, an integrally bladed disc forging, a wheel, a tube or a shaft.

Preferably the component comprises a metal, a ceramic, a metal matrix composite or a polymer matrix composite.

Preferably the apparatus comprises a tank containing an acoustic coupling liquid, the component is immersed in the acoustic coupling liquid.

Preferably the first transducer is a piezoceramic transducer, an electromagnetic acoustic transducer or a transducer comprising a laser.

Alternatively the first transducer is an electromagnetic eddy current transducer.

The present invention will be more fully described by way of example with reference to the accompanying drawings in which:—

Figure 1:
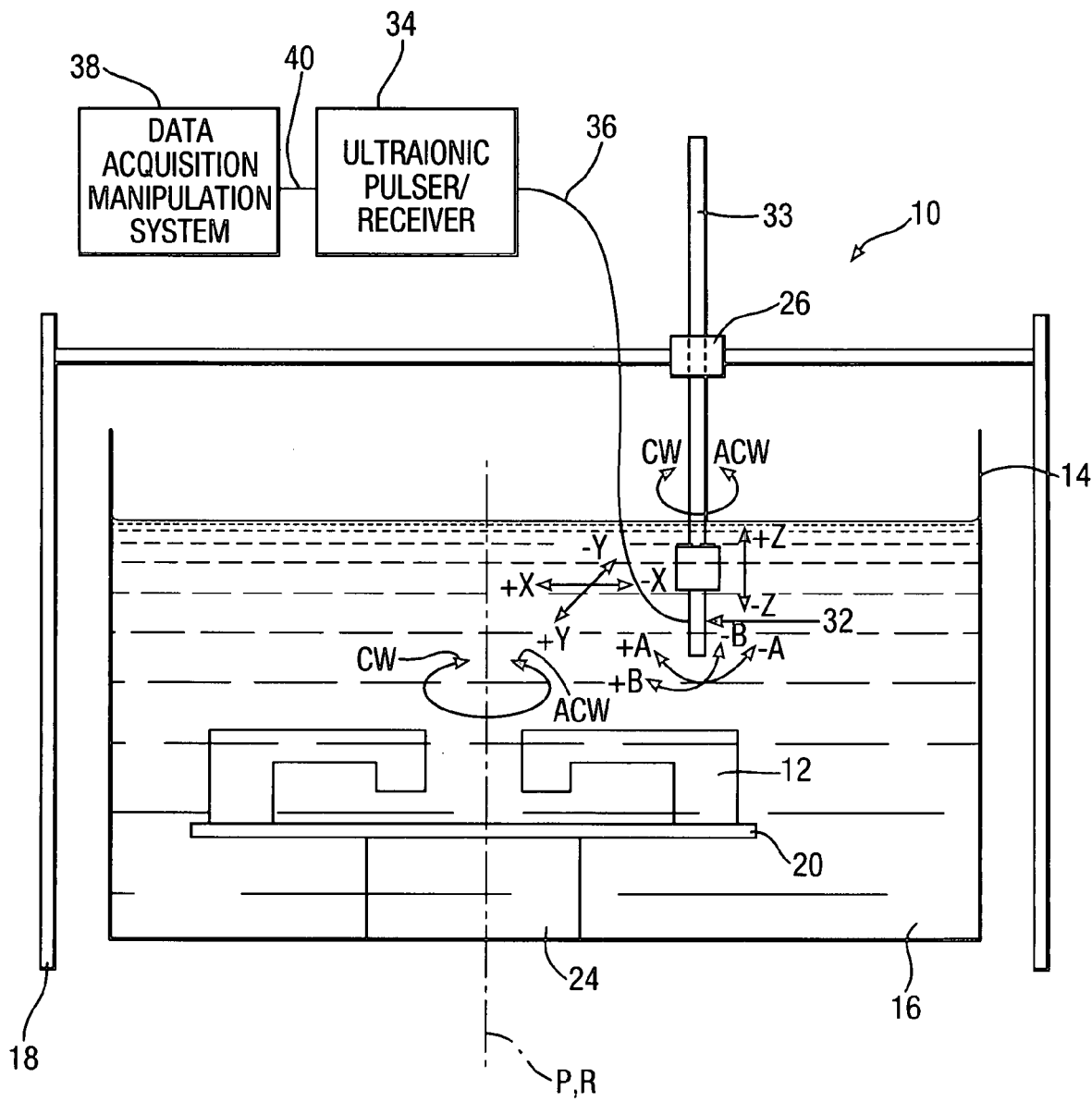
FIG. 1 is a side view of an apparatus for ultrasonically inspecting a rotationally symmetrical component according to the present invention.
Figure 2:
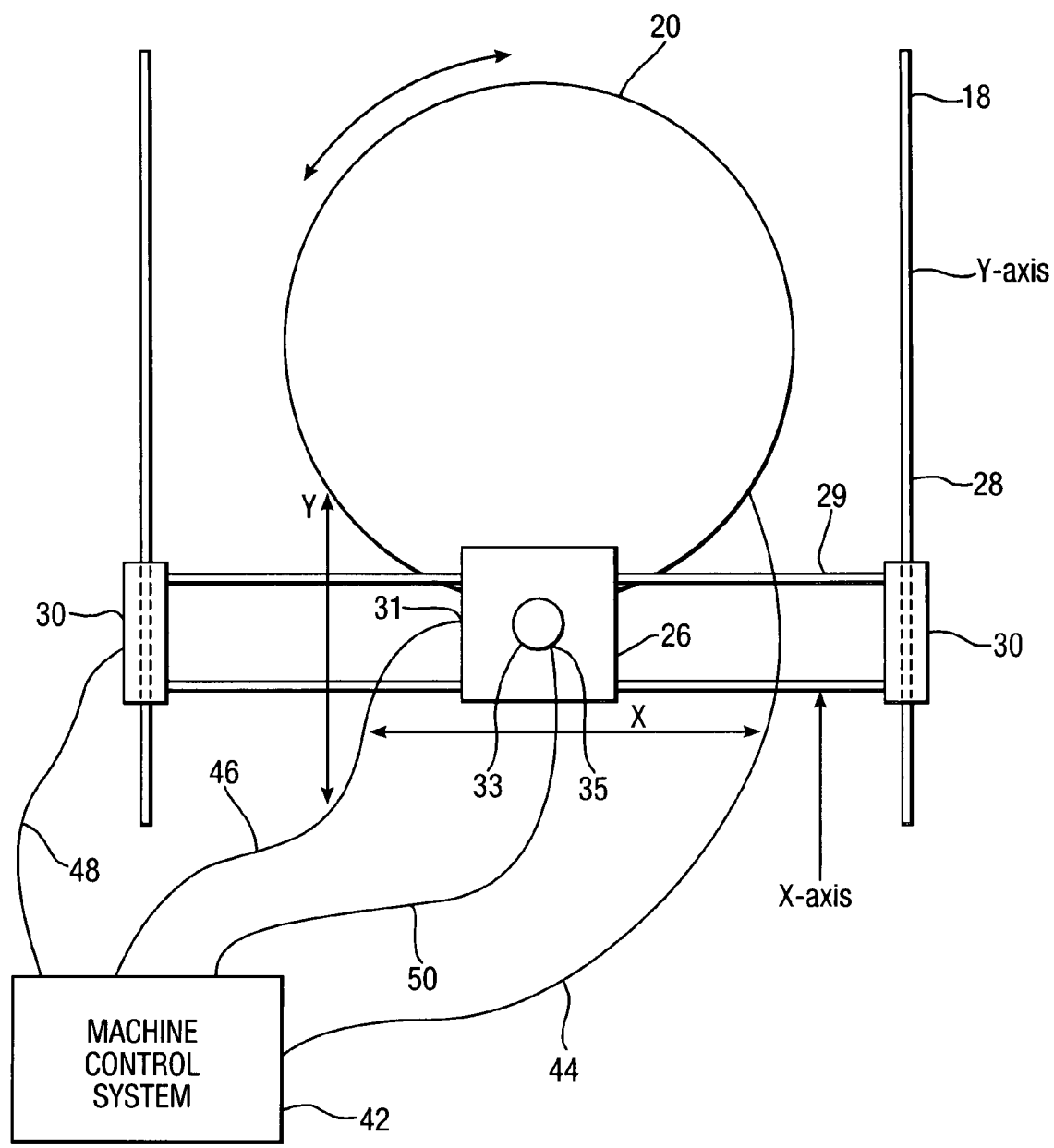
FIG. 2 is a plan view of the apparatus for ultrasonically inspecting a component shown in FIG. 1.

An apparatus 10, as shown in FIGS. 1 and 2, for ultrasonically inspecting a rotationally symmetrical component 12 comprises a tank 14 containing a liquid 16 and a frame 18. A rotatable turntable 20 and means 24 are provided to rotate the turntable 20. The means 24 to rotate the turntable 20 is preferably a motor directly driving the turntable, but alternatively the means to rotate the turntable 20 may be a motor indirectly driving the turntable via a belt, or a chain. The rotationally symmetrical component 12 is immersed in the liquid 16 in the tank 14 and is positioned on the turntable 20 such that the axis of rotational symmetry P of the component 12 coincides with the axis of rotation R of the turntable 20.

The frame 18 is provided with a carriage 26, which is movable along first and second tracks 28 and 29 on the frame 18 and means 30 and 31 are provided to move the carriage 26 along the tracks 28 and 29. The tracks 28 and 29 are arranged perpendicularly to enable movement in a Y-axis and an X-axis respectively. The carriage 26 carries an ultrasonic transducer 32 on a member 33 and means 35 are provided to move the member 33 towards or away from the turntable 20 and component 12 in a direction perpendicularly to the tracks 28 and 29 in a Z-axis. The member 33 may also be rotated. The means to move the carriage 26 and to move the member 33 may be motors or hydraulic, pneumatic or electric pistons and cylinders etc.

The ultrasonic transducer 32 transmits and receives ultrasonic signals and the ultrasonic transducer is electrically connected to an ultrasonic signal pulser and receiver 34 by an electric cable 36 and is electrically connected to an ultrasonic signal analyser and display 38 by the ultrasonic signal pulser and receiver 34 and electric cables 36 and 40. The ultrasonic signal analyser and display 38 comprises a computer e.g. a personal computer. The ultrasonic transducer 32 may also have A and B normalising axes. The ultrasonic pulser and receiver 34, sometimes called an ultrasonic flaw detector, comprises a very high gain amplifier and a timing trigger. There is also a controller 42 electrically connected to the motor 24 via a cable 44, electrically connected to the motor 31 via a cable 46, electrically connected to the motor 30 via a cable 48 and electrically connected to the motor 35 via a cable 50 to provide signals to move the carriage 26 and the member 33.

In operation the controller 42 sends signals to the motor 24 such that the turntable 20 is rotated about its axis of rotation for one complete revolution while the carriage 26 and transducer 32 are at a first radial position of the component 12. During the rotation of the turntable 20 the ultrasonic transducer 32 is supplied with ultrasonic signals from the ultrasonic signal pulser and receiver 34 and the ultrasonic transducer 32 injects ultrasonic signals through the liquid 16 and into the component 12. The ultrasonic transducer 32 detects reflected ultrasonic signals from the component 12 and supplies ultrasonic signals to the ultrasonic signal analyser 38 via the ultrasonic signal pulser and receiver 34. The ultrasonic signal analyser 38 stores the ultrasonic signals.

The controller 42 sends signals to the motors 30 and/or 31 such that the carriage 26 is moved along the tracks 28 and 29 on the frame 18 and the turntable 20 is rotated about its axis of rotation for one complete revolution while the carriage 26 and transducer 32 are at a second radial position of the component 12. During the rotation of the turntable 20 the ultrasonic transducer 32 is supplied with ultrasonic signals from the ultrasonic signal pulser and receiver 34 and the ultrasonic transducer 32 injects ultrasonic signals through the liquid 16 and into the component 12. The ultrasonic transducer 32 detects reflected ultrasonic signals from the component 12 and supplies ultrasonic signals to the ultrasonic signal analyser 38 via the ultrasonic signal pulser and receiver 34. The ultrasonic signal analyser 38 stores the ultrasonic signals.

The carriage 26 is repeatedly moved along the tracks 28 and 29 on the frame 18 and the turntable 20 is rotated for one complete revolution so that the ultrasonic inspector 32 ultrasonically inspects all the radial positions of the component 12.

The turntable 20 is rotated around its axis of rotation at a constant speed of rotation of between 5 rpm and 30 rpm preferably between 20 rpm and 30 rpm.

The ultrasonic signal analyser 38 stores and analyses all the detected ultrasonic signals from the ultrasonic transducer 32. The ultrasonic signal analyser 38 manipulates the ultrasonic signals and displays the ultrasonic signals on the display 38. The ultrasonic signal is displayed on the display 38 as a chart of rotational position against time with ultrasonic signal amplitude displayed as a grey scale or artificial colour for each scan increment. The ultrasonic signal analyser 38 analyses the ultrasonic signals and differentiates by separation of ultrasonic signals with and without rotational symmetry, highlighting ultrasonic signals that have no rotational symmetry and have an amplitude above a predetermined amplitude as a potential defect, such as a crack, a fissure, an inclusion or a flaw etc. Geometric features, such as changes in changes in cross-sectional thickness, in the component have rotational symmetry. A defect, such as a crack, a fissure, an inclusion or a flaw etc, in the component however occurs at a discrete location in the component and therefore lacks rotational symmetry and is easily distinguished.

The ultrasonic signal analyser 38 detects a defect by detecting a cluster of pixels above the predetermined amplitude. True defects possess a finite length/area whereas external interference, e.g. electrical noise, are instantaneous spikes. The ultrasonic signal analyser 38 detects a cluster of pixels above the predetermined amplitude and containing n consecutive pixels where n>1, where n is a fixed integer.

True defects are automatically detected and separated from background signals due to changes in cross-sectional thickness or noise, without the need for laborious manual scanning of edge features. Any indication of a defect may be manually viewed by an inspector, after the scan and this allows an inspector to operate several ultrasonic inspection systems.

Following an ultrasonic inspection of one surface of a component, the ultrasonic signal analyser 38 displays a table of all detected defect clusters, showing an ID number, e.g. component serial no, face ID and number) position and maximum ultrasonic signal amplitude. The ultrasonic signal analyser 38 allows an inspector to view the maximum A-scan ultrasonic signal for each defect cluster. The ultrasonic signal analyser 38 records the inspector decision for each defect cluster. All the detected defect clusters are assessed by an inspector and the decision recorded before the inspection process progresses to the next stage. The inspector saves the resultant A-scan and the relative positions of the ultrasonic transducer and the component.

The opposite surface of the component may be inspected in the same manner as above.

Figure 3:
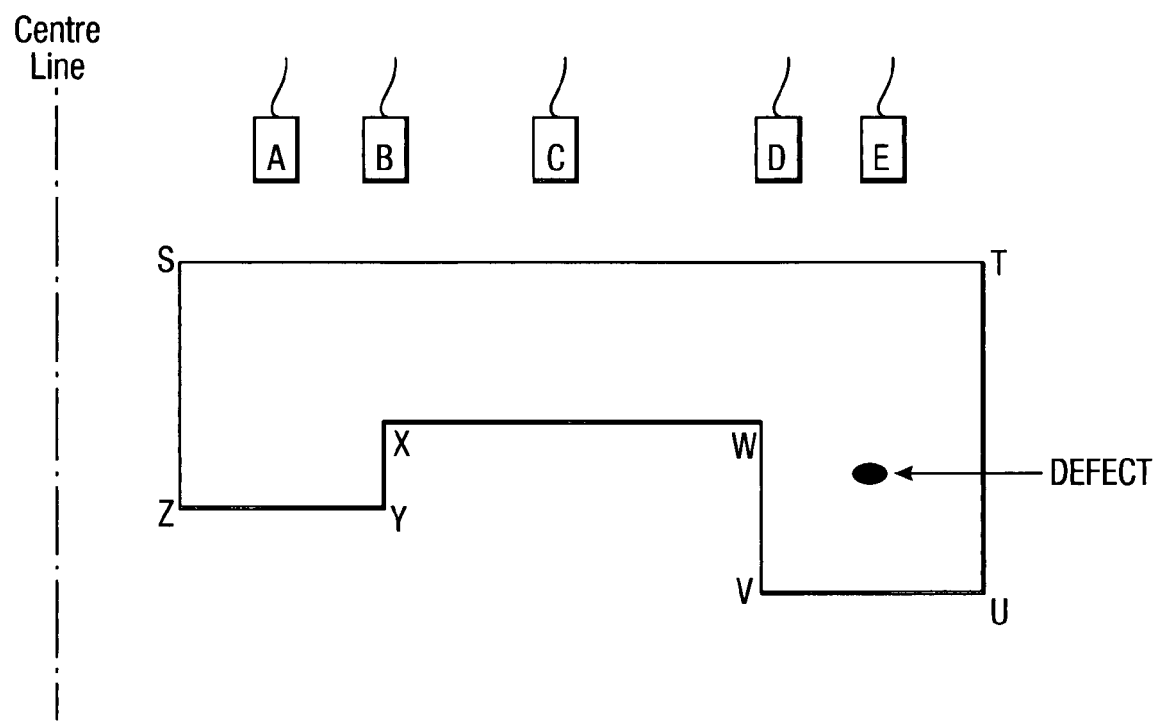
FIG. 3 is a schematic section through a half of the rotationally symmetrical component showing the ultrasonic transducer at six positions relative to the component.

FIG. 3 is a schematic cross-section of a half of a turbine disc forging 50 and the radial positions A, B, C, D and E of an ultrasonic transducer 52 at different times in the ultrasonic inspection procedure.

Figure 4:
FIG. 4 is a display of a detected ultrasonic signal from the ultrasonic transducer at three radial positions in a component.
Figure 4:
Figure 4:
Figure 4:
Figure 4:

FIG. 4 is a chart showing the detected ultrasonic signals for one revolution of the ultrasonic transducer 52 at each of the radial positions A, B and C.

Figure 5:
FIG. 5 is a display of a detected ultrasonic signal from the ultrasonic transducer at a further two radial positions in a component.
Figure 5:
Figure 5:
Figure 5:
Figure 5:
Figure 5:

FIG. 5 is a chart showing the detected ultrasonic signals for one revolution of the ultrasonic transducer 52 at each of the radial positions D and E.

It is clearly seen from FIGS. 4 and 5 that at radial position A there are reflections from the near surface ST and the far surfaces ZY and at radial position C there are reflections from the near surface ST and the far surface XW of the component 52. It is clearly seen from FIGS. 4 and 5 that at radial position B there are reflections from the near surface ST and the far surfaces ZY and XW and at radial position D there are reflections from the near surface ST and the far surfaces XW and UV of the component 52. It is clear from FIG. 5 that at radial position E there are reflections from the near surface ST and the far surface UV and a reflection from a defect. The reflections from the near and far surfaces are rotationally symmetrical, but the reflection from the defect is not rotationally symmetrical and this allows the ultrasonic signal analyser to filter the ultrasonic signals and to distinguish the ultrasonic signals from defects from ultrasonic signals from changes in cross-sectional thickness or ultrasonic signals from other rotationally symmetrical features.

The advantages of the present invention are that it automatically caters for changes in cross-sectional thickness of the component. It decreases the time to perform an ultrasonic inspection of a component and eliminates most of the manual intervention by an inspector. It provides a permanent record of the ultrasonic inspection in terms of response level, defect position, defect depth and ultrasonic signal characteristics. It removes the need for manual scans because it simplifies and clarifies the recording, displaying and interpretation of data at component edges, cross-sectional thickness changes and sloping faces. It is suitable for on-line remote technical surveillance, to overview data collected at another inspection site without the need to be present during an inspection.

The ultrasonic inspection may be used with several revolutions of the ultrasonic transducer at each radial position, e.g. first pass at 90°, second pass at 85° and third pass at 95° relative to the surface.

The present invention is applicable to the ultrasonic inspection of turbine discs, turbine disc forgings, compressor discs, compressor disc forgings, fan discs, fan disc forgings, integrally bladed discs, e.g. discs with blades integrally formed, or machined, with the disc or discs with blades frictionally welded, diffusion bonded, e beam or laser welded to the discs, bladed disc forgings, bladed rings, e.g. rings with blades integrally formed, or machined, with the ring or rings with blades frictionally welded, diffusion bonded, e beam or laser welded to the rings, bladed ring forgings, wheels, tubes or shafts.

The present invention is applicable to the ultrasonic inspection of metal components, ceramic components, metal matrix composite component or polymer matrix composite components.

Although the present invention has been described with reference to the use of a single transducer to transmit the ultrasonic signal into the component and to detect the reflected ultrasonic signal, it may be possible to use a second transducer to detect the reflected ultrasonic signal. Although the present invention has been described with reference to detecting a reflected ultrasonic signal it may also be possible to provide a second transducer to detect an ultrasonic signal transmitted through the component.

The present invention is also applicable using other acoustic couplant methods such as water jet probes, oil or gel contact methods or remote methods such as high amplitude airborne pulse or laser generated ultrasound or electromagnetic acoustic transducers (EMATS).

Although the present invention has been described with reference to the use of ultrasonic inspection of a component, the present invention may also be applied to electromagnetic eddy current inspection of a component.

It may be possible to inspect a component without rotational symmetry, such as a square cross-section component or a rectangular cross-section component, for example a plate for a solid fan blade or a hollow fan blade. In this instance there will be relative x and y movement between the component and the transducer.

I claim:

1. A method of ultrasonically inspecting a component comprising transmitting an ultrasonic signal from a first ultrasonic transducer into a component having rotational symmetry, detecting the reflected, or transmitted, ultrasonic signal by a second ultrasonic transducer, producing relative rotation between the rotationally symmetrical component and the first and second transducers, producing relative radial motion between the rotationally symmetrical component and the first and second transducers to scan the whole of a surface of the rotationally symmetrical component, storing and analysing all the detected ultrasonic signal, analysing the detected ultrasonic signal by monitoring for ultrasonic signals having an amplitude above a predetermined amplitude and not having rotational symmetry, detecting a defect in the component by detecting a cluster of pixels above the predetermined amplitude, providing an indication that any detected ultrasonic signals above the predetermined amplitude and not having rotational symmetry is a potential defect in the component and providing a permanent record of the ultrasonic inspection in terms of response level, defect position and defect depth.

2. A method as claimed in claim 1 comprising rotating the component about its axis of symmetry.

3. A method as claimed in claim 1 comprising moving the first and second transducers radially relative to the component.

4. A method as claimed in claim 1 wherein the first transducer and the second transducer are the same transducer operating in pulse echo mode.

5. A method as claimed in claim 1 wherein the component is a turbine disc, a turbine disc forging, a compressor disc, a compressor disc forging, a fan disc, a fan disc forging, an integrally bladed disc, an integrally bladed disc forging, a wheel, a tube or a shaft.

6. A method as claimed in claim 1 wherein the component comprises a metal, a ceramic, a metal matrix composite or a polymer matrix composite.

7. A method as claimed in claim 1 comprising immersing the component in an acoustic coupling liquid.

8. A method as claimed in claim 1 wherein the first transducer is a piezoceramic transducer, an electromagnetic acoustic transducer or a transducer comprising a laser.

9. A method as claimed in claim 1 comprising producing relative rotation at a constant speed.

10. A method as claimed in claim 9 comprising producing relative rotation at a constant speed between 3 rpm and 30 rpm.

11. A method as claimed in claim 10 comprising producing relative rotation at a constant speed between 20 rpm and 30 rpm.

12. A method as claimed in claim 1 comprising displaying all detected defect clusters by showing component ID number, position of defect clusters and maximum ultrasonic signal amplitude.

13. An apparatus for ultrasonically inspecting a component comprising a first ultrasonic transducer for transmitting an ultrasonic signal into a component having rotational symmetry, a second ultrasonic transducer for detecting the reflected, or transmitted, ultrasonic signal, means to produce relative rotation between the rotationally symmetrical component and the first and second transducers, means to produce relative radial motion between the rotationally symmetrical component and the first and second transducers to scan the whole of a surface of the rotationally symmetrical component, means to store and analyse all the detected ultrasonic signals, means to analyse the detected ultrasonic signal by monitoring for ultrasonic signals having an amplitude above a predetermined amplitude and not having rotational symmetry, means to detect a defect by detecting a cluster of pixels above the predetermined amplitude, means to provide an indication that any detected ultrasonic signals above the predetermined amplitude and not having rotational symmetry is a potential defect in the component and means to provide a permanent record of the ultrasonic inspection in terms of response level, defect position and defect depth.

14. An apparatus as claimed in claim 13 wherein the means to produce relative rotation comprises means to rotate the component about its axis of symmetry.

15. An apparatus as claimed in claim 13 wherein the means to produce relative radial movement comprises means to move the first and second transducers radially relative to the component.

16. An apparatus as claimed in claim 13 wherein the first transducer is the second transducer.

17. An apparatus as claimed in claim 13 wherein the component is a turbine disc, a turbine disc forging, a compressor disc, a compressor disc forging, a fan disc, a fan disc forging, an integrally bladed disc, an integrally bladed disc forging, a wheel, a tube or a shaft.

18. An apparatus as claimed in claim 13 wherein the component comprises a metal, a ceramic, a metal matrix composite or a polymer matrix composite.

19. An apparatus as claimed in claim 13 comprising a tank containing an acoustic coupling liquid, the component is immersed in the acoustic coupling liquid.

20. An apparatus as claimed in claim 13 wherein the first transducer is a piezoceramic transducer, an electromagnetic acoustic transducer or a transducer comprising a laser.

21. An apparatus as claimed in claim 13 comprising means to display all detected defect clusters by showing the component ID, position of defect clusters and maximum ultrasonic signal amplitude.

22. A method of ultrasonically inspecting a component comprising transmitting an ultrasonic signal from a first ultrasonic transducer into a component having rotational symmetry, detecting the reflected, or transmitted, ultrasonic signal by a second ultrasonic transducer, producing relative rotation at a constant speed between the rotationally symmetrical component and the first and second transducers, producing relative radial motion between the rotationally symmetrical component and the first and second transducers to scan the whole of a surface of the rotationally symmetrical component, storing and analysing all the detected ultrasonic signal, analysing the detected ultrasonic signal by monitoring for signals having an amplitude above a predetermined amplitude and not having rotational symmetry, providing an indication that any detected ultrasonic signals above the predetermined amplitude and not having rotational symmetry is a potential defect in the component and providing a permanent record of the ultrasonic inspection in terms of response level, defect position and defect depth.

23. An apparatus for ultrasonically inspecting a component comprising a first ultrasonic transducer for transmitting an ultrasonic signal into a component having rotational symmetry, a second ultrasonic transducer for detecting the reflected, or transmitted, signal, means to produce relative rotation at a constant speed between the rotationally symmetrical component and the first and second transducers, means to produce relative radial motion between the rotationally symmetrical component and the first and second transducers to scan the whole of a surface of the rotationally symmetrical component, means to store and analyse all the detected ultrasonic signal, means to analyse the detected ultrasonic signal by monitoring for ultrasonic signals having an amplitude above a predetermined amplitude and not having rotational symmetry, means to provide an indication that any detected ultrasonic signals above the predetermined amplitude and not having rotational symmetry is a potential defect in the component and means to provide a permanent record of the ultrasonic inspection in terms of response level, defect position and defect depth.

* * * * *